(12) United States Patent
Alland et al.

(10) Patent No.: US 6,461,817 B1
(45) Date of Patent: Oct. 8, 2002

(54) NON-COMPETITIVE CO-AMPLIFICATION METHODS

(75) Inventors: David Alland, Dobbs Ferry; Fred R. Kramer, Riverdale, both of NY (US); Amy Piatek, Brookline, MA (US); Sanjay Tyagi, New York, NY (US); Jacqueline Vet, Malden (NL)

(73) Assignee: The Public Health Research Institute of the City of New York, Newark, NJ (US)

( * ) Notice: Subject to any disclaimer, the term of this patent is extended or adjusted under 35 U.S.C. 154(b) by 0 days.

(21) Appl. No.: 09/508,343

(22) PCT Filed: Sep. 11, 1998

(86) PCT No.: PCT/US98/19182

§ 371 (c)(1),
(2), (4) Date: Oct. 20, 2000

(87) PCT Pub. No.: WO99/13113

PCT Pub. Date: Mar. 18, 1999

Related U.S. Application Data

(60) Provisional application No. 60/058,729, filed on Sep. 12, 1997.

(51) Int. Cl.⁷ .......................... C12Q 1/68; C12P 19/34; C07H 21/02; C07H 21/04
(52) U.S. Cl. .................... 435/6; 435/91.2; 536/23.1; 536/24.3
(58) Field of Search .................. 435/6, 91.2; 536/23.1, 536/24.3; 935/76, 77, 78

(56) References Cited

U.S. PATENT DOCUMENTS

| | | |
|---|---|---|
| 5,409,818 A | 4/1995 | Davey et al. |
| 5,455,166 A | 10/1995 | Walker |
| 5,538,848 A | 7/1996 | Livak et al. |
| 5,556,771 A | 9/1996 | Shen et al. |
| 5,925,517 A | 7/1999 | Tyagi et al. |
| 6,103,476 A | 8/2000 | Tyagi et al. |

OTHER PUBLICATIONS

Gibson et al., Genome Research 6 (10) : 995–1001 (1996).*
Tyagi et al., Molecular Beacons: Probes that Fluoresce upon Hybridization, Nature Biotechnology 14: 303–308, 1996.
Ursi et al., Utility of an Internal control for the polymerase chain reaction, APMIS 100: 635–639, 1992.
Vet et al., Multiplex detection of four pathogenic retroviruses using molecular beacons, Proc. Natl. Acad. Sci. USA 96: 6394–6399, 1999.
Guatelli et al., Isothermal, in vitro amplification of nucleic acids by a multienzyme reaction modeled after retroviral replication, Proc. Natl. Acad. Sci. USA 87: 1874–1878, 1990.
Keller et al., Detection of Hepatitis B Virus DNA in Serum by Polymerase Chain Reaction Amplification and Microtiter Sandwich Hybridization, Journal of Clinical Microbiology vol. 28, No. 6: 1411–1416, 1990.
Bonnet et al., Thermodynamic basis of the enhanced specificity of structured DNA probes, Proc. Natl. Acad. Sci. USA 96: 6171–6176, 1999.
Heid et al., Real Time Quantitative PCR, Genome Research 6: 986–994, 1996.

* cited by examiner

*Primary Examiner*—Ethan C. Whisenant
(74) *Attorney, Agent, or Firm*—Fish & Richardson PC

(57) ABSTRACT

Non-competitive, quantitative amplification assay methods, including assays employing amplification by the polymerase chain reaction (PCR) process, for accurately measuring levels of target nucleic acid and sequences in samples and for ascertaining the relative amounts of cross-hybridizing alleles and mutants.

16 Claims, 4 Drawing Sheets

NON-COMPETITIVE CO-AMPLIFICATION METHODS

This application is the national phase of PCT/US98/19182, filed Sep. 11, 1998, which claims the priority of U.S. provisional patent application No. 60/058,729, filed Sep. 12, 1997.

This invention was made with government support under grant numbers NO1 AI 45244 and RO1 AI 35015, both awarded by the National Institutes of Health. The United States government has certain rights in the invention.

This invention relates to amplification assays to detect nucleic-acid targets.

BACKGROUND OF THE INVENTION

This application relates to assays employing exponential amplification of a target sequence. The target sequence may be RNA or DNA. By "amplification of a target sequence," we mean to include amplification of the target sequence itself and also amplification of a transcript thereof, as when an RNA target sequence is amplified by first creating a DNA transcript with reverse transcriptase and then amplifying the DNA transcript. By "exponential amplification" we mean an amplification reaction or reactions that generate products ("amplicons") that include both plus strands and complementary minus strands.

In referencing target sequences, control sequences, amplicons and probes, we mean to include both plus and minus strands. Thus, it will be understood that when referring to cross hybridization of a control sequence with a target sequence or to cross hybridization of two target sequences during amplification, we are referring to hybridization of the plus strand of one to the minus strand of the other. Similarly, when we refer to hybridization of a probe to a target sequence, we mean to include hybridization of the probe to either the plus-strand or the minus strand of the target sequence itself or to an amplicon, that is a plus-strand copy or minus-strand copy of the target sequence.

Several reaction schemes are used in assays employing amplification of a target sequence. The most widely used is the polymerase chain reaction (PCR) process. It will be used herein for presentation of the specifics of the prior art and the specifics of this invention. However, it will be understood that this invention also applies to other reaction schemes, including nucleic acid sequence-based amplification (NASBA), transcription-mediated amplification (TMA), self-sustained sequence replication (3SR) (Guatelli et al. (1990)) and strand displacement amplification (SDA) (Walker et al. (1992)).

The polymerase chain reaction process is well known. It is the most widely used technique for amplifying DNA and RNA (RT-PCR) targets, including amplification as part of assays to detect the presence of DNA and RNA targets for many purposes, including, for example, in vitro diagnostics, genetic analyses, forensics, food and agricultural testing, and parentage testing. PCR is used for detection even at the level of a single cell (in situ PCR).

Quantitative PCR assays are also well known. Quantitative PCR assays for DNA and RNA have been widely used to study disease processes (see, for example, Clementi et al., 1993). One type of quantitative PCR assay involves simultaneously amplifying control molecules and samples containing (or suspected to contain) a target sequence. Receptacles containing known amounts of control molecule are thermally cycled with receptacles, most commonly tubes or wells or slides, containing the unknown amount of target. In addition to the pair of PCR primers for the target, a pair of PCR primers is required for each control molecule. Following amplification, the amounts of amplified products (amplicons) are compared. See generally Clementi el al., 1994 and Kahn et al., 1992. Partly due to variation in amplification efficiency among primers, only relative quantitation between samples is possible.

Another type of quantitative PCR assay is quantitative-competitive PCR (QC PCR). In this method a control molecule which is similar to but ultimately distinguishable from the target sequence competes with the target sequence for the same pair of primers. Following competitive amplification, the two products synthesized (amplicons) are distinguished, for example, by size using gel electrophoresis. See generally Wang et al., 1989 and Becker-Andre, 1991. While permitting more than relative quantitation between samples, QC PCR has inherent disadvantages and limitations. Post-amplification manipulation is required. This complicates the assay, decreases throughput, increases labor, and risks contamination of untested samples by amplicon carryover. Assay design is complicated by the need for a competitor-control that amplifies with an efficiency very close to that of the target unknown. For reasonable quantitation, most QC PCR assays are performed in multiple tubes containing serial dilutions, of the competitor-control, typically five-fold dilutions, but in some assays two-fold dilutions for better accuracy. Differences in amplification efficiency between the target and the competitor-control usually compel analysis during the exponential phase of amplification, because errors become too large during the subsequent linear phase. (Mullis and Faloona, 1987). Precision is limited, varying a minimum of fifty percent between parallel assays.

A more recently developed type of quantitative PCR assay has been called the 5'-nuclease assay and "real-time PCR." See generally, Gibson et al., 1996; Heid et al., 1996; Gelfand et al., 1993; and Livak et al., 1996. This method utilizes detector probes that are linear DNA sequences labeled with two different fluorescent dyes, for example, a reporter dye such as FAM and a quenching dye such as TAMRA. Commercial kits from the Applied Biosystems Division of The Perkin-Elmer Corporation (Foster City, Calif. (U.S.A.)) are available under the trademark TaqMan™. When not hybridized to target (original unknown or amplicon) the quenching dye partially quenches the reporter dye. During the annealing step of a PCR cycle, the probes hybridize to the target sequence, and during the extension step of the PCR cycle, the probes are cleaved by the 5'→3' nucleolytic activity of DNA polymerase. Cleavage releases the reporter dye from the quenching dye, resulting in an increase in fluorescence. Fluorescence can be monitored throughout the PCR amplification. An instrument available from the Applied Biosystems Division of The Perkin-Elmer Corporation, the ABI PRISM 7700, monitors fluorescence in 96 tubes simultaneously in real time. An improved probe suitable for real-time PCR has been developed. See Tyagi and Kramer, 1996. This probe, referred to as a "molecular beacon", possesses a stem-and-loop structure, has a higher signal-to-background ratio than linear probes and also has improved allele discrimination. During the annealing step of a PCR cycle, molecular beacon probes hybridize to the target sequence and fluoresce, but during the extension step of the PCR cycle, the probes leave the target and do not interfere with polymerization.

Due to sample-to-sample variations in PCR efficiency, only data from the early, exponential amplification phase should be used. That limited data permits a determination of the PCR cycle number at which fluorescence becomes detectable above background (the cycle threshold). The cycle threshold decreases in proportion to the logarithm of initial target concentration. A standard curve can be generated from the cycle thresholds of a dilution series of known starting concentrations of target, and the cycle threshold of a sample containing an unknown amount of target sequence can be compared to the standard curve in order to determine the amount of target sequence present in the sample. Real-time PCR has a wider dynamic range than QC PCR. Importantly, it does not suffer from the serious disadvantages resulting from opening tubes after amplification. It utilizes homogeneous detection with a probe that is added prior to amplification. Nevertheless, accuracy is limited due to variations in amplification efficiency. For example, Gibson et al. (1996) performed real-time PCR using two sets of tubes. Each set contained triplicate two-fold dilutions of a control molecule and a fixed amount of unknown. Despite use of averaged triplicate samples of two-fold dilutions to create a standard curve for cycle thresholds and use of averaged triplicate samples of unknown, quantitation of the unknown in the two separate experiments differed by thirty percent.

SUMMARY OF THE INVENTION

An aspect of this invention is nucleic acid hybridization assays that do not require post-amplification manipulation, that include at least two sequences which are subject to the same reaction kinetics, and that include homogenous detection utilizing interactively labeled hybridization probes.

Another aspect of this invention is quantitative, homogeneous PCR assays wherein the precision is significantly improved over the thirty-percent variability of real-time PCR.

Another aspect of this invention is homogenous nucleic acid hybridization assays, including especially PCR assays, to detect amounts of two co-amplifiable, cross hybridizable targets in a sample, either the relative amount of one to the other or absolute amounts of both, with high precision.

These and other aspects of this invention will be apparent from the description, including the figures, which follow.

Two or more different sequences that cross hybridize, as during the annealing step of a PCR reaction, can be co-amplified using a single set of primers. By "cross hybridize" we mean that the amplicons of each sequence hybridize not only to themselves but also to amplicons of the other sequences. For such sequences, the amplifications of the sequences are linked; they follow the same reaction kinetics and act as a single amplicon. We refer to this as non-competitive amplification. It differs from competitive amplification, such as in QC PCR (wherein two sequences compete for a single set of primers and follow different reaction kinetics, and where one sequence may grow at the expense of the other). The difference is profound with respect to quantitation and relative quantitation in homogeneous detection assays in which tubes are not opened for further manipulation following amplification.

Detection in the assays of this invention utilizes what we refer to as "dual-labeled hybridization probes" by which we mean hybridization probes having at least two interactive labels, whose signal varies depending on whether the probe is hybridized to a strand or free-floating in a single-stranded conformation. Fluorescent labels are preferred and will be used to illustrate and explain such probes. Such probes are suitable for homogeneous assays, because separation of bound probes from unbound probes is not required, as is required when traditional fluorescently labeled probes not having interactive labels are used. As stated above, we are aware of two different types of dual-labeled hybridization probes. One is a linear probe known as the TaqMan™ probe, described in Heid et al., 1996; Gibson et al., 1996; Livak et al., 1996; and Gelfand et al., 1993; all of which are incorporated herein in their entireties. The probe is a linear oligonucleotide complementary to a non-primer portion of a sequence to be amplified (that is, it hybridizes between the primers, for example, PCR primers). The probe is labeled at two nucleotides removed from each other with a reporter dye such as FAM and a quenching dye such as TAMRA. When the probe is not hybridized to a strand, the quencher partially quenches the fluorescence of the reporter. When the probe hybridizes to the target sequence, as during the annealing step of PCR, it sits in the path of the DNA polymerase that will generate a copy, as in the extension step of PCR. The DNA polymerase cleaves the probe, thereby permanently severing the reporter from the quencher. Such probes have a limited ability to "allele discriminate," by which we mean to distinguish between two sequences that differ by as little as a single nucleotide.

A second type of dual-labeled hybridization probe useful in assays according to this invention is a hairpin probe in which a probe sequence is a loop and flanking arm sequences form a double-stranded stem. Each arm contains one of the at least two interactive labels, typically a fluorophore and a quencher. Fluorescently labeled molecular beacons undergo a fluorogenic conformational change when they hybridize to their target. A fluorescent moiety is covalently linked to the end of one arm and a quenching moiety is covalently linked to the end of the other arm. The stem keeps these two moieties in close proximity to each other, causing the fluorescence of the fluorophore to be quenched by energy transfer. Since the quencher is a non-fluorescent chromophore that emits the energy that it receives from the fluorophore as heat, fluorescence does not occur. When the probe encounters a target molecule, it forms a probe-target hybrid that is longer and more stable than the stem hybrid. The rigidity and length of the probe-target hybrid precludes the simultaneous existence of the stem hybrid. Consequently, the molecular beacon undergoes a spontaneous conformational reorganization that forces the stem hybrid to dissociate and the fluorophore and the quencher to move away from each other, restoring fluorescence. Fluorescence increases as much as 900-fold when these probes bind to their target. Various label pairs may be used, including among others the fluorophore EDANS and the quencher DABCYL. These probes, called "molecular beacons", and their preparation and use in homogenous, real-time PCR assays are described in Tyagi and Kramer, 1996, and in Tyagi et al., 1996, each of which is incorporated herein in its entirety. The ability of a molecular beacon probe containing a probe section 15 nucleotides long flanked by complementary arms, each 5 nucleotides long, to effectively discriminate between targets differing by a single nucleotide is described. We prefer molecular beacon probes for use as dual-labeled probes in assays according to this invention. Specifically we prefer fluorescently labeled molecular beacons having a probe sequence 7–25 nucleotides in length and flanking arm sequences 3–8 nucleotides in length.

One embodiment of an assay utilizing non-competitive amplification of a target sequence, preferably PCR amplification, is a quantitative assay for an unknown amount of a target sequence. A co-amplifier DNA strand which will cross hybridize with the target sequence is utilized in known amount. We sometimes refer to this as a control molecule. A probe specific for the target sequence and a probe specific for the co-amplifier are used. Preferred probes are fluorescer/quencher-labeled molecular beacon probes (Tyagi and Kramer (1996)) which are capable of discriminating against a single base-pair mismatch. With these probes, the control molecule may be identical to the target sequence except at one nucleotide. Other dual-labeled probes whose signal is a function of the amount of target (original target sequence or amplicon), such as TaqMan™ probes described above, can also be used. In many instances a series of PCR amplification reactions containing a dilution series of the control molecule DNA will be used.

We have discovered that the ratio of the target sequence to the control molecule is constant throughout the PCR reaction, including in the linear phase. Thus, the ratio can be determined at any cycle in which the fluorescences of both probes are above the background level. More preferably, the ratio can be determined at many cycles and averaged to provide an extremely accurate quantitation. Persons in the art will understand how to calculate the ratios.

Various combinations of probes can be employed, for example: a probe specific for the control (preferably complementary to a portion of the control sequence that differs by at least one nucleotide, preferably one nucleotide, from the corresponding portion of the target sequence of the unknown) and a probe specific for both the unknown and the control; a probe specific for the unknown and a probe specific for both the unknown and the control; a probe specific for the control and a probe specific for the unknown; and a probe specific for the control, a probe specific for the unknown and a third probe specific for both the control and the unknown (obviously complementary to a sequence that occurs in both the control and the unknown). In each of these embodiments one obtains a ratio or ratios from which the concentration of unknown target can be readily calculated. Especially preferred is the use of three probes: one specific for the unknown target sequence, one specific for the control, and one specific for both, that is, designed to hybridize equally to both the target and the control. Use of three probes provides additional data and an internal control. An instrument such as the ABI PRISM 7700, described above, can be programmed to make computations automatically. However, the method is so accurate that a single reading during, or at the end of, the PCR amplification can be used.

Another embodiment of non-competitive PCR assays is an assay to detect the ratio of two closely related target sequences, such as alleles or mutants, for example, drug-resistant mutant pathogens. Amplicons containing genetic alleles differing by a single nucleotide and amplicons containing drug-resistant mutants differing from a wild-type pathogen, for example bacterium or virus, by a single nucleotide will cross hybridize as required for non-competitive amplification. When two unknowns co-amplify in a non-competitive PCR reaction, the ratio of the progeny amplicons derived from the first unknown to progeny amplicons derived from the second unknown remains constant throughout the amplification, including the linear phase. We have shown, for example, that one can distinguish as little as two percent of mutant DNA in an otherwise wild-type DNA population. It will be appreciated from the preceding discussion that this embodiment can be precisely quantitative by using a control in a known amount.

Unless otherwise defined, all technical and scientific terms used herein have the same meaning as commonly understood by one of ordinary skill in the art to which this invention belongs. Although methods and materials similar to those described herein can be used in the practice or testing of the present invention, suitable methods and materials are described below. All publications, patent applications, patents, and other references mentioned herein are incorporated by reference in their entirety. In case of conflict, the present application, including definitions, will control. In addition, the materials, methods, and examples described herein are illustrative only and not intended to be limiting.

Other features and advantages of the invention, e.g., accurate quantitation of pathogens in patients will be apparent from the following detailed description, from the drawings and from the claims.

DETAILED DESCRIPTION

Figure 1:
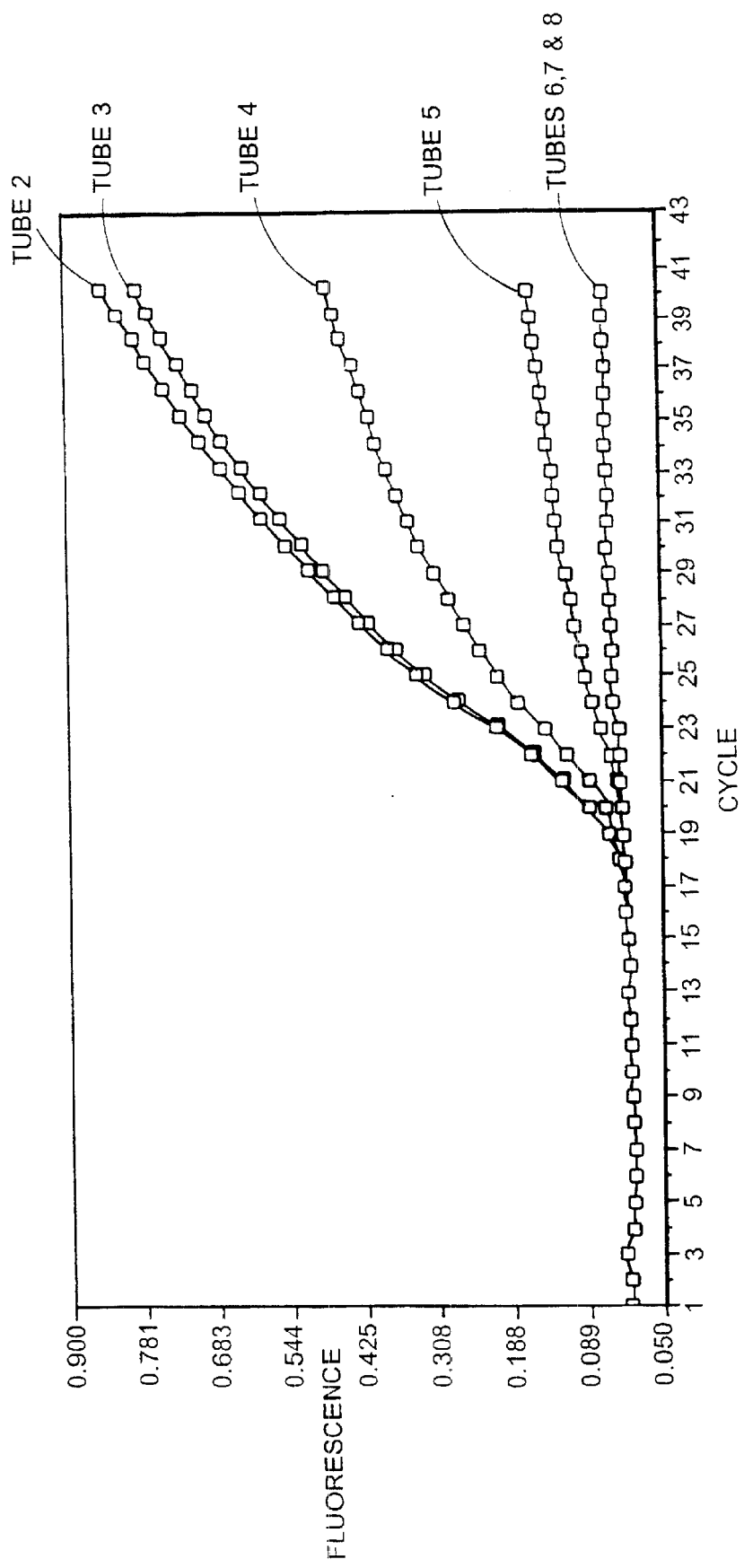
FIG. 1 is a line graph showing the PCR amplification kinetics of a *Mycobacterium tuberculosis* strain M235 rpo B gene sequence present at a different concentration, in each reaction tube, relative to that of an rpo B gene sequence from *M. tuberculosis* strain J24. The rpo B gene sequences from the 2 strains differ by a single nucleotide at position 561.

In non-competitive amplification according to this invention, amplification of at least two closely related, cross hybridizing molecules occurs as a single amplicon with a single set of kinetics. The individual amplifications are linked. Two, three, four or five molecules can take part in a single PCR reaction, for example. The fraction of the amplicons derived from each parent molecule remains constant throughout the amplification.

Using competitive amplification, quantitation is performed by calculating the ratio of unknown product to the known control and extrapolating back to the number of molecules of unknown target in the original sample. The reaction is described by the equation:

i $C/U = C_o(1+effC)^n/U_o(130\ effU)^n$, where $C_o$ is the initial amount of control molecules, $U_o$ is the initial amount of unknown molecules, C is the final amount of control molecules, U is the final amount of unknown molecules, eff is the efficiency of amplification (effC being the efficiency of amplification of the control molecule and effU being the efficiency of amplification of the unknown), and n is the number of PCR cycles (adapted from Clementi et al., 1994).

Using non-competitive amplification according to this invention, effu and effc are the same, so the equation reduces to:

$C/U = Co/Uo$, where
- Co is the initial concentration of co-amplifier (which may be a control, an allele or a mutant, for example) and
- C is the final concentration of the co-amplifier.

When Co is known, as in a quantitation assay embodiment, quantitative PCR is simple and highly accurate throughout a PCR amplification.

To accommodate probes having differing fluorescence intensities, which is the usual case when different fluorophores are used, quantitation includes use of a factor k to correct for the difference. Using molecular beacon probes, we have demonstrated that k remains constant throughout a PCR amplification. The factor k can thus be represented as n=ku, where n is the fluorescence of one molecular beacon and u is the fluorescence of the other molecular beacon. The relationship can be used in several ways. When u is the measured fluorescence of a molecular beacon that is specific for an unknown and n is the measured fluorescence of a molecular beacon specific for a co-amplifier, $$C/U = n/ku,$$

or $$U_o = C_o ku/n$$

When u is the measured fluorescence of a molecular beacon that is specific for an unknown and n is the measured fluorescence of a molecular beacon specific for both the unknown and a co-amplifier, the concentration equation becomes
ti $C/U = (n-ku)/ku,$ or $$Uo = Coku/(n-ku)$$

Since k will have been calculated from a PCR reaction with known amounts of unknown and co-amplifier, for example, and $C_o$ is known, only u and n need be measured in a quantitation assay to give $U_o$ very precisely. Accuracy is limited only by the initial measurement of $C_o$ and the chosen instrument's ability to measure u and n.

The following examples are meant to illustrate the invention and not to limit it.

EXAMPLES

Example 1

Unexpected Kinetics of PCR in a DNA Sample is Due to the Presence of a Mixture of Wild-type and Mutant Sequence The experiments that provide the basis for this invention were stimulated by an unexpected observation. The inventors regularly perform molecular beacon PCR assays on *M. tuberculosis* rpo B targets. Molecular beacon-PCR of one DNA sample using a molecular beacon specific to wild-type rpo B sequence gave consistently unexpected results. This sample had a cycle threshold similar to equal molar concentrations of control DNA. However, fluorescence intensity increased more slowly after the cycle threshold than predicted by its concentration and reached a plateau at approximately 50of the expected value. It seemed possible that this result was due to the presence in the sample of a mixture of wild type and mutant sequences, where the mutant sequence inhibited molecular beacon fluorescence due to wild type sequence.

To explore this possibility, the following experiment was performed. *M. tuberculosis* strains M235 and J24 have identical DNA rpo B gene sequences except for a single G to T nucleotide substitution at codon 516. A molecular beacon specific for the M235 rpo B sequence was constructed. This molecular beacon was found only to fluoresce in the presence of its appropriate target. Eight PCR reactions using a primer pair which would amplify both M235 and J24 molecules were performed. The total amount of DNA in each tube was kept constant, but contained a different ratio of M235 and J24 DNA. Each reaction tube contained identical amounts of PCR reaction mixture and the molecular beacon specific to M235 rpo B. Tube 1 contained 10 ng of M235, tube 2 contained 9.9 ng of M235 and 0.1 ng of J24, tube 3 contained 9 ng of M235 and 1 ng of J24, tube 4 contained 5 ng of each strain, tube 5 contained 1 ng of M235 and 9 ng of J24, tube 6 contained 0.1 ng of M235 and 9.9 ng of J24, tube 7 contained 10 ng of J24, and tube 8 contained no chromosomal DNA and served as a molecular beacon only control. The molecular beacon specific to M235 generated a series of fluorescent curves. Data obtained with tubes 2–8 are shown in FIG. 1. Each curve started at approximately the same cycle and the slope and the final plateau fluorescence values of each curve decreased in parallel to the fraction of M235 DNA present at the start of the PCR reaction. These findings were unexpected since, under normal conditions, the cycle threshold increases approximately 3 cycles with each ten-fold dilution of M235 DNA. In this experiment, the cycle thresholds for tubes 2 through tubes 6 (9.9 ng to 0.1 ng of M235, a 99-fold dilution), appeared nearly identical. Furthermore, in contrast to what occurs under normal conditions (i.e., the initial slope of increased fluorescence subsequent to the cycle threshold is similar for all DNA dilutions), under the conditions of this experiment, the slopes of the fluorescence curves for each reaction differed over a 45 degree range.

Figure 2:
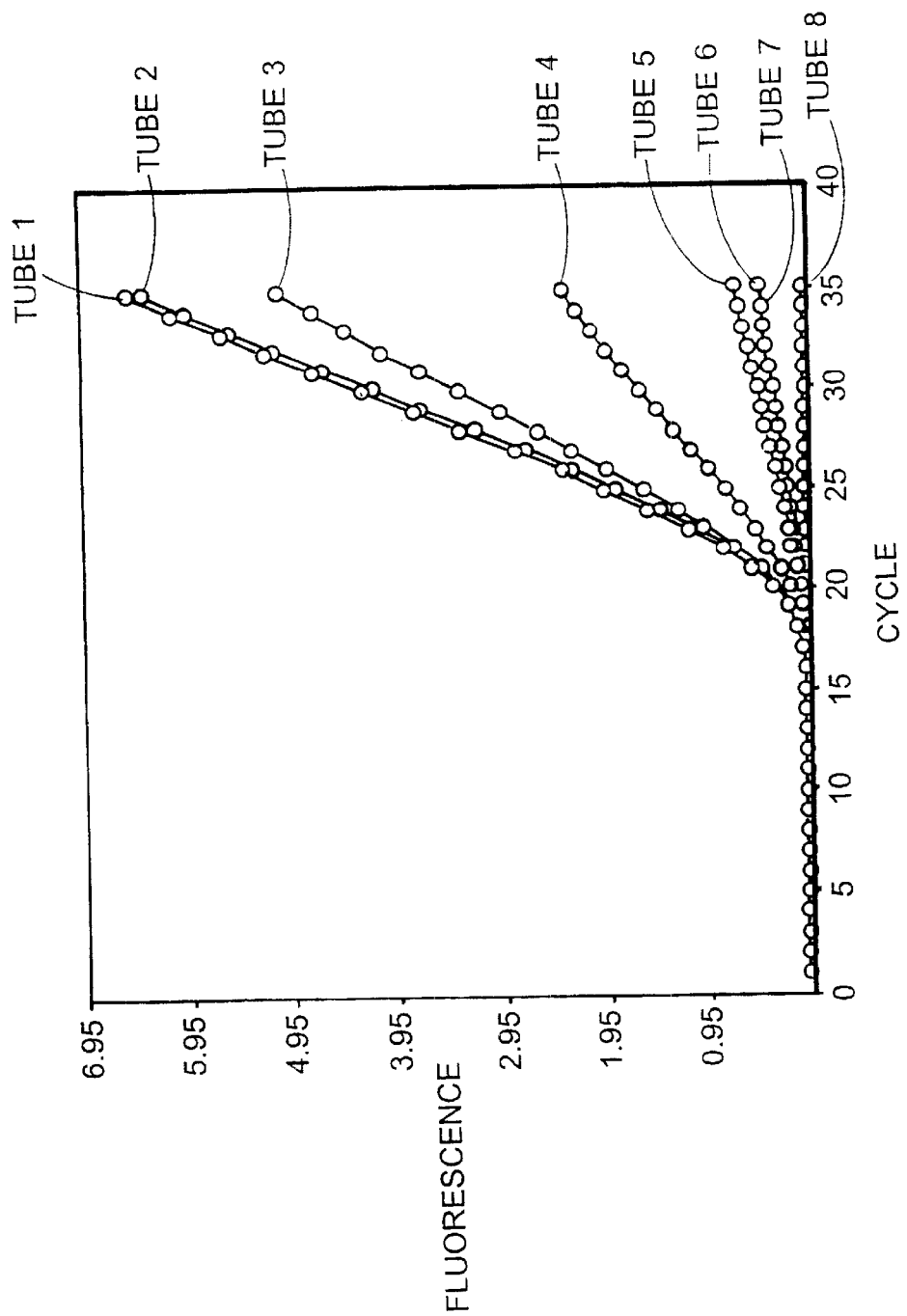
FIG. 2 is a line graph from an experiment carried out under the same conditions as that shown on FIG. 1, except that five-fold higher concentrations of the PCR primers were used.

The decrease in M235 fluorescence may be partly explained if J24 DNA, which was also present in the PCR reaction, acted as a competitor for primers and other reagents. If two amplicons share primers in QC PCR, when the more abundant species reaches the plateau phase, amplification of the minority species is forced to plateau as well, due to exhaustion of shared primers. However, such competition should also increase the M235 cycle threshold. In the current experiment, the cycle thresholds for all samples were apparently the same but were decreased relative to that predicted by DNA concentration. FIG. 2 shows data obtained from an experiment carried out as described for that shown in FIG. 1, except that a five-fold higher concentration of primers was used. Comparison of FIGS. 1 and 2 indicates that the kinetics of amplification in PCRs which were prevented from entering a plateau phase by using the higher concentration of primers were essentially the same as those of PCRs containing the lower concentration of primers. This result excluded the possibility that the unexpected kinetics of the reaction was due to competition for the primers. Additional experiments were performed in which the amount of M235 was kept constant and varying amounts of "competitor" J24 were added. As little as 2% J24 DNA caused a measurable decrease in M235 fluorescence.

The amplification kinetics described above can only be explained if PCRs containing both M235 and J24 are no longer thought of as containing two distinct molecules with individual PCR amplification kinetics. Instead, J24 and M235 amplicons behave as interacting molecules with linked kinetics and amplification efficiencies. This stands in contrast to existing QC PCR assays where competitor and unknown amplifications behave as separate reactions which have roughly equivalent amplification efficiencies due to similar target sequences and shared primers. In conventional QC PCR assays, competitor and unknown amplification efficiencies are never identical. This is demonstrated experimentally by the fact that quantitation is always found to be most accurate when competitor and unknown are present in equal ratios. When one target is present in excess, differences in amplification efficiency are augmented, which lead to increasingly large errors. However, molecular beacons can distinguish between amplicons which use the same PCR primers and differ from each other by only one base pair. The above findings suggest that under these conditions, both molecules amplify as one amplicon. Early in the reaction, when primers are in vast excess, primer annealing and effM 235 (the efficiency of amplification of M235) and effJ24 (the efficiency of amplification of J24) are identical; later in the reaction, when PCR product begins to accumulate and template/template reannealing influences amplification efficiency, M235/J24 heteroduplex reannealing occurs as frequently as M235/M235 and J24/J24 homoduplex reannealing. EffM235 and effJ24 are always identical because PCR amplification of M235 and J24 are firmly linked throughout the exponential, linear and plateau phases of the PCR cycle regardless of the initial relative concentrations of each target.

Example 2

The Kinetics of Linked and Unlinked PCR are Different

Figure 3:
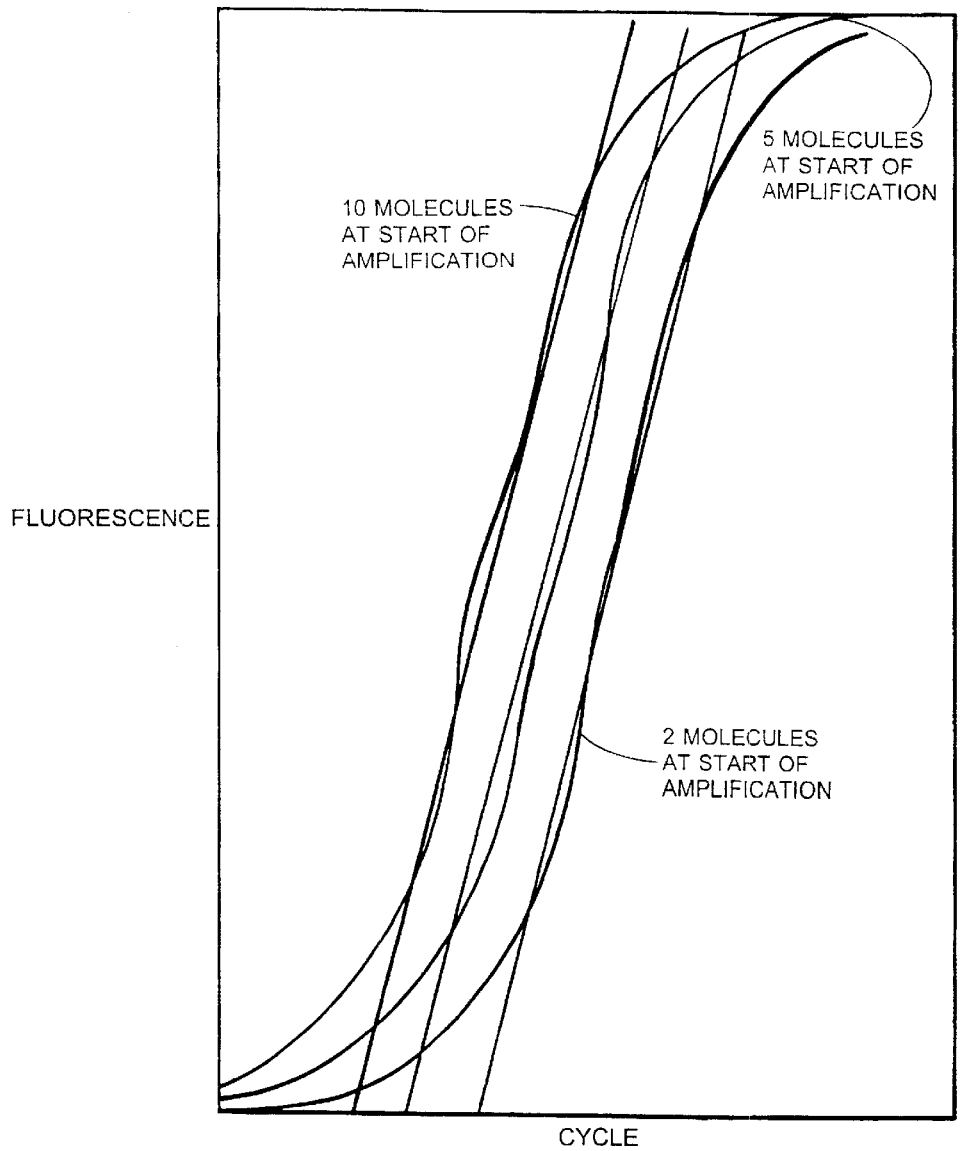
FIG. 3 is a line graph showing the theoretical kinetics of amplification in three individual PCR reactions containing different numbers of template molecules.
Figure 4:
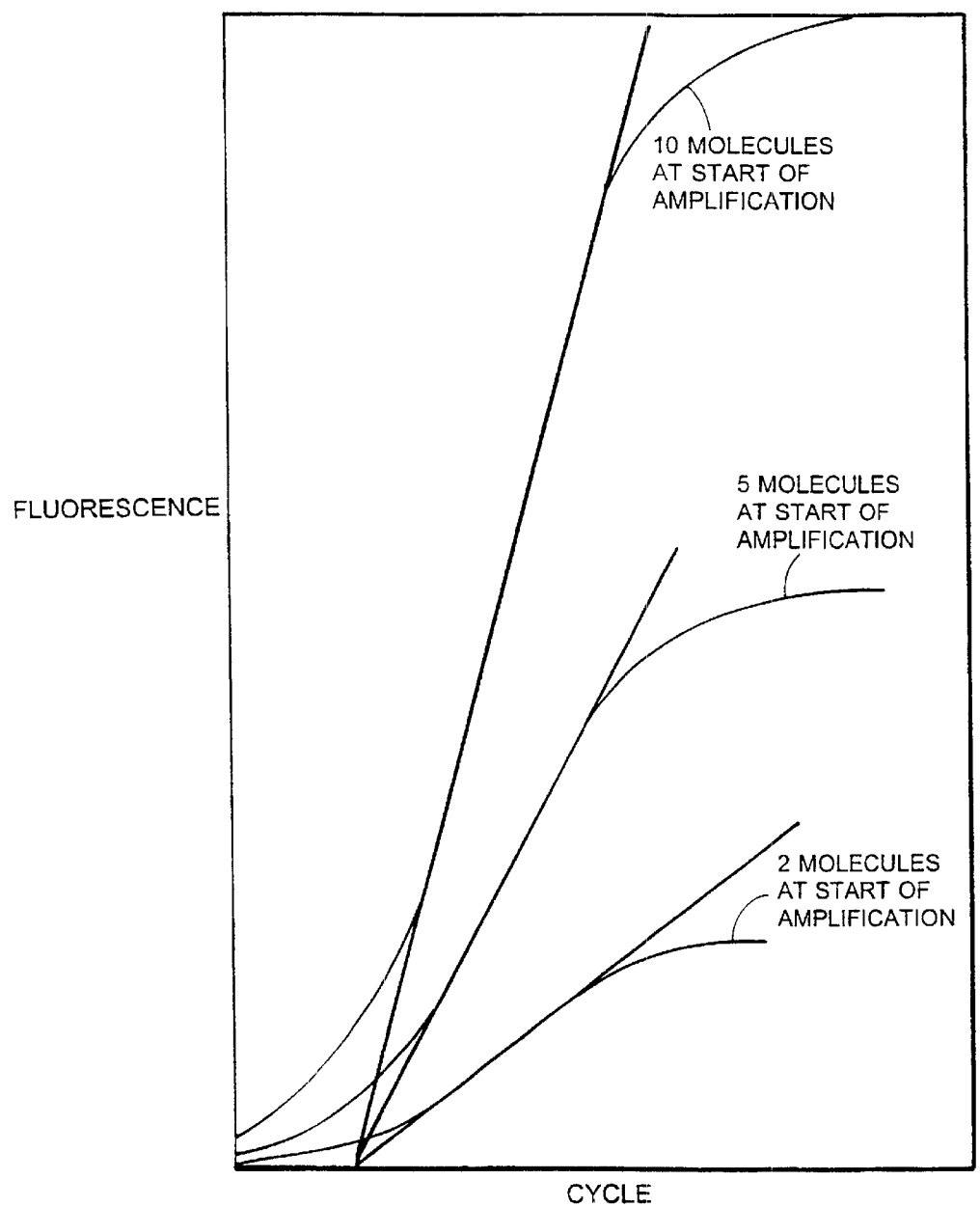
FIG. 4 is a line graph showing the theoretical kinetics of amplification in a single PCR reaction containing the same number of template molecules as in all three PCR reactions depicted in FIG. 3.

The differences between linked and unlinked PCR reactions are illustrated in FIGS. 3 and FIG. 4 showing idealized PCR reactions. In FIG. 3, the top curve demonstrates PCR amplification starting with ten molecules. The molecules amplify exponentially for four cycles, increase linearly for two cycles, then enter a lag phase ultimately ending in a plateau. The middle and bottom curves show how a PCR reaction with the same kinetics would appear if independent reactions were begun with one half (middle curve) or one fifth (bottom curve) the number of target molecules (i.e., five molecules and two molecules, respectively). Each PCR reaction is independent. The linear and plateau phases begin after a given number of target molecules have been generated; each reaction leaves the exponential phase after a different number of PCR cycles, and the curves rise in parallel with each other. The model presented in FIG. 3 was confirmed experimentally in PCR reactions in which serial dilutions of DNA in separate tubes without competitors were amplified.

The model presented in FIG. 4 illustrates how the identical number of molecules would amplify if they were part of the same PCR reaction. As in FIG. 3, the top curve of FIG. 4 shows the amplification of ten molecules which amplify exponentially for four cycles, linearly for two cycles, then enter a lag phase, ending in a plateau. In this case, however, all curves represent the same PCR reactions. The middle and bottom curves show how the same amplification would appear if only one half or one fifth of the molecules were visualized. In the top curve, the linear phase starts after four cycles due to the limiting effect of primers and template reannealing. In the middle and bottom curves, the linear phase is also entered after four cycles because every identical molecule in the PCR reaction is under the same constraints. Unlike the situation in FIG. 3, the ratio of the progeny amplicons derived from the starting subset represented in each curve to the total number of amplicons remains the same at every stage of the PCR, and the curves no longer rise in parallel. For example, one half of the molecules at the start of the reaction will amplify to produce one half of the molecules present at each stage of the reaction. The same data would be produced if three molecular beacons could be constructed so that one could visualize all of the molecules (top curve), one could visualize one half of the molecules (middle curve), and one could visualize one fifth of the molecules (bottom curve). A striking aspect of FIG. 4 is that all linear phases of the PCR reaction extrapolate to a single point (as shown in this case by the lines intersecting at cycle number 2). This phenomenon must occur whenever linked reactions are plotted by molecular number (fluorescence) and PCR cycle.

The findings (FIGS. 1 and 2) of the experiment described above in Example 1 can readily be explained in light of these models. J24 and M235 act as identical molecules amplifying as one linked PCR reaction with identical amplification efficiencies. Because the molecular beacon detects M235 but not J24, only a fraction of the total reaction is visualized. Each curve represents the fraction of the total PCR reaction which is due to the M235 amplicon. The curves appear to have similar cycle thresholds (FIGS. 1 and 2). However, this is an illusion caused by the scale of the PCR plot and the sensitivity of the assay which detects fluorescence above baseline only when the PCR reaction is nearing the linear phase. Each curve appears to originate from the same cycle threshold because the linear phase of each curve extrapolates back to a single point. The observed decrease in fluorescence with progressively fewer M235 DNA molecules also exactly parallels what is predicted by FIG. 4. The level of fluorescence at any cycle is directly proportional to the number of M235 molecules at the start of the PCR reaction.

These findings lead to the following conclusions. When two DNA molecules of adequate length differ by only one base pair, not in the primer region, they amplify as linked PCR reactions with identical amplification efficiencies. In such circumstances, the two targets are no longer "competitors" but rather are "co-amplifiers" participating equally in a non-competitive reaction. Using co-amplifiers of this type, the equation $C/U = C_o(1+effC)^n/U_o(1+effU)^n$ can be reduced to $C/U = C_o/U_o$ (where $C_o$ is now the initial concentration of the co-amplifier, and C is the final concentration of the co-amplifier). Because $C_o$ is usually known, and both C and U can be measured, quantitative PCR using co-amplifiers is simple and highly accurate in all stages of the PCR reaction. One additional discovery has made it possible to measure C and U in the same PCR tube using molecular beacons (see Example 3).

Example 3

Use of More Than One Molecular Beacon Allows Accurate Quantitation of an Amplicon Molecular beacons made with different fluorophores but constructed to hybridize with the same PCR amplicon, can be used simultaneously in the same tube of a PCR reaction, and the ratio of their fluorescence is constant. This ratio does not change at any point in the PCR reaction (exponential or linear) and does not vary with subsequent assays or with different initial concentrations of template, as long as the same mixture of multiple molecular beacons is used.

Two molecular beacons were constructed, each designed to hybridize to different sequences in a 134 base pair amplicon of the *M. tuberculosis* rpo B gene. One molecular beacon was labeled with fluorescein; the other was labeled with Texas red. Reactions were carried out in five different tubes, each containing identical amounts of both molecular beacons in PCR reaction buffer, but different amounts of chromosomal *M. tuberculosis* DNA strain M235. PCR reactions were performed for 50 cycles. The fluorescence spectra of each molecular beacon was simultaneously measured throughout the PCR reaction. Each molecular beacon generates different amounts of fluorescence but the fluorescent curves rise in parallel through the course of the PCR reaction. A ratio of fluorescence of each molecular beacon can be calculated at a given PCR cycle. This ratio remains constant at any cycle number up to the 50 cycles performed. The fluorescent ratio remains identical when two different experiments are compared. This demonstrates that for a mixture of two molecular beacons which hybridize to the same target, a fluorescence ratio can be derived. This ratio can be combined with a measure of the fluorescence of one molecular beacon to calculate the fluorescence of the second molecular beacon.

REFERENCES

Becker-Andre M. Quantitative Evaluation of mRNA levels. Meth. Molec. Cell Biol. 1991 2:189–201.

Clementi M, Patrizia B, Manzin A, Menzo S. Competitive polymerase chain reaction and analysis of viral activity at the molecular level. GATA 1994; 11:1–6.

Gelfand et al., "Homogeneous Assay System Using The Nuclease Activity Of A Nucleic Acid Polymerase", U.S. Pat. No. 5,210,015, (1993).

Guatelli et al. (1990) Proc. Natl. Acad. Sci. USA 87:1874.

Gibson U E M, Heid C A, Williams P M. A novel method for real time quantitative RT-PCR Genome research. 1996; 6:995–1001.

Heid C A, Stevens J, Livak K J, Williams P M. Real-time quantitative PCR. Genome Research. 1996; 6:986–994.

Khan I, Tabb T, Garfield R E, Grover A K. Neurosci. Lett. 1992; 147:114–117.

Livak et al., "Method For Detecting Nucleic Acid Amplification Using Self-Quenching Fluorescence Probe", U.S. Pat. No. 5,538,848, (1996).

Mullis, K. B. and Faloona, F. A. (1987) Methods in Enzymology, Vol. 155:335–350.

Tyagi S. and Kramer F. R., Molecular beacons: probes that fluoresce upon hybridization. Nature Biotechnology 1996; 14:303–308.

Tyagi et al. (1996), "Detectably Labeled Dual Conformation Oligonucleotide Probes, Assays and Kits, European Patent Application EP 0745 690A2.

Walker et al. (1992) Nucleic Acids Res. 20:1691.

Wang A, Dolye M, Mark D F. Proc. Natl. Acad. Sci. USA. 1989; 86:9717–9721.

We claim:

1. A non-competitive, quantitative amplification assay for a target DNA sequence, comprising the steps of:
   providing a reaction mixture for an amplification of said target DNA sequence that includes of a sample suspected to contain said target DNA sequence, reagents for amplifying said target DNA sequence, and a known quantity of a DNA control molecule which has a different sequence from said target sequence, which hybridizes to said target DNA sequence or its complement, and which is co-amplifiable with said target DNA sequence in a single amplification reaction having a single set of reaction kinetics for both the target DNA sequence and the DNA control molecule;
   co-amplifying said control molecule and said target DNA sequence, if present, in said single amplification reaction to produce amplicons of both;
   detecting said amplicons in solution with dual-labeled hybridization probes capable of causing a fluorescent signal to be generated in response to hybridizing to sequences complementary to sequences in the probes, said probes including at least two probes selected from the group consisting of:
   (a) a first probe for said target sequence or its complement but not for said control molecule or its complement;
   (b) a second probe for said control molecule or its complement but not for said target sequence or its complement; and
   (c) and a third probe for both the target sequence or its complement and the control molecule or its complement,
   wherein binding of said amplicons to said probes is detectable by signals generated by said probes; and
   determining the starting quantity of said target DNA sequence utilizing the ratio of signals from said at least two probes during at least one point during said amplification reaction.

2. The assay of claim 1, wherein the amplification reaction is the polymerase chain reaction (PCR).

3. The assay of claim 1, wherein the amplification reaction is strand displacement amplification (SDA).

4. The assay of claim 1, wherein the amplification reaction is self-sustained sequence amplification (3SR).

5. The assay of claim 1, wherein the amplification reaction is target-mediated amplification (TMA).

6. The assay of claim 1, wherein said probes are molecular beacon probes.

7. The assay of claim 6 wherein at least one of the molecular beacon probes discriminates between targets that differ by a single nucleotide.

8. An assay for determining the relative quantities in a sample of at least two different nucleic acid sequences, a first sequence and a second sequence, that are cross hybridizable and co-amplifiable in a single amplification reaction having a single set of reaction kinetics for both of said sequences, comprising:
   co-amplifying said sequences in said single amplification reaction;
   detecting said amplicons in solution with dual-labeled hybridization probes capable of causing a fluorescent signal to be generated in response to hybridizing to sequences complementary to sequences in the probes, said probes including at least two probes selected from the group consisting of:
   (a) a first probe for said first sequence or its complement but not for said second sequence or its complement;
   (b) a second probe for said second sequence or its complement but not for said first sequence or its complement; and
   (c) a third probe for both said first sequence or its complement and said second sequence or its complement,
   wherein binding of said amplicons to said probes is detectable by signals generated by said probes; and
   determining the ratio of said at least two sequences in said sample utilizing a ratio based on said signals of said at least two probes during at least one point during said amplification reaction.

9. The assay of claim 8, wherein the amplification reaction is the polymerase chain reaction (PCR).

10. The assay of claim 8, wherein the amplification reaction is strand displacement amplification (SDA).

11. The assay of claim 8, wherein the amplification reaction is self-sustained sequence amplification (3SR).

12. The assay of claim 8, wherein the amplification reaction is target-mediated amplification (TMA).

13. The assay of claim 8, wherein said probes are molecular beacon probes.

14. The assay of claim 13, wherein at least one of the molecular beacon probes discriminates between targets that differ by a single nucleotide.

15. The assay of claim 1 wherein said at least two probes are included in said reaction mixture.

16. The assay of claim 8 wherein said at least two probes are included in said reaction mixture.

* * * * *